ically the entire page

US009623063B2

United States Patent
Dal Monte et al.

(10) Patent No.: US 9,623,063 B2
(45) Date of Patent: *Apr. 18, 2017

(54) **EXTRACTS FROM *AJUGA REPTANS* CELL LINES, THEIR PREPARATION AND USE**

(75) Inventors: Renzo Dal Monte, Creazzo (IT);
Roberto Dal Toso, Creazzo (IT);
Anacleto Minghetti, Milan (IT);
Nicoletta Crespi Perellino, Milan (IT);
Giovanna Pressi, Monteforte D'Alpone (IT)

(73) Assignee: I.R.B. ISTITUTO DI RICERCHE BIOTECNOLOGICHE S.r.l., Altavilla, Vicentina (IT)

( * ) Notice: Subject to any disclaimer, the term of this patent is extended or adjusted under 35 U.S.C. 154(b) by 1109 days.

This patent is subject to a terminal disclaimer.

(21) Appl. No.: 11/455,505

(22) Filed: Jun. 19, 2006

(65) Prior Publication Data
US 2007/0015262 A1     Jan. 18, 2007

(30) Foreign Application Priority Data

Jun. 20, 2005   (EP) .................................... 05425441
Aug. 8, 2005    (EP) .................................... 05425585

(51) Int. Cl.
| | |
|---|---|
| *A61K 36/53* | (2006.01) |
| *A61K 8/60* | (2006.01) |
| *A61K 8/97* | (2017.01) |
| *A61K 31/70* | (2006.01) |
| *A61K 31/702* | (2006.01) |
| *A61Q 7/00* | (2006.01) |
| *A61Q 11/00* | (2006.01) |
| *A61Q 19/00* | (2006.01) |
| *A61Q 19/02* | (2006.01) |
| *A61Q 19/08* | (2006.01) |
| *C07H 15/18* | (2006.01) |

(52) U.S. Cl.
CPC ............. *A61K 36/53* (2013.01); *A61K 8/602* (2013.01); *A61K 8/97* (2013.01); *A61K 31/70* (2013.01); *A61K 31/702* (2013.01); *A61Q 7/00* (2013.01); *A61Q 11/00* (2013.01); *A61Q 19/00* (2013.01); *A61Q 19/004* (2013.01); *A61Q 19/02* (2013.01); *A61Q 19/08* (2013.01); *C07H 15/18* (2013.01); *A61K 2800/782* (2013.01)

(58) Field of Classification Search
None
See application file for complete search history.

(56) References Cited

U.S. PATENT DOCUMENTS 5,882,664 A * 3/1999 Soma et al. .................. 424/401
6,538,019 B1 * 3/2003 Nakajima et al. ............ 514/449
6,544,965 B2 * 4/2003 Minghetti et al. ............. 514/61

FOREIGN PATENT DOCUMENTS

| EP | 1118617 | 8/2005 |
| JP | 07-223962 | 8/1995 |
| WO | 2004/033673 | 4/2004 |
| WO | WO 2004/033673 A2 * | 4/2004 |
| WO | 2006/100101 | 9/2006 |

OTHER PUBLICATIONS

Terahara et al., Triacylated anthocyanins from *Ajuga reptans* Flowers and Cell Cultures, 1996, Phytochemistry, 42, 199-203.*
Ozeki et al., http://pcp.oxfordjournals.org/cgi/content/abstract/26/5/903☐☐ prior art date 1985.*
Tomoko et al. "Phenylethanoid glycodides from Stachys riederi" Natural medicines; 1340-3443; vol. 48 (1994), No. 1, p. 32-38.
Li Ji Rui-Chang "Antioxidative and chelating activities of phenylpropanoid glycosides". Zhongguo yaoli xuebao; vol. 18(1997), 1, p. 77-80.
Pan J et al "Pharmacological activities and mechanisms of natural phenylpropanoid glycosides" Pharmazie; 0031-7144; vol. 58 (2003), 11, p. 767-775.
Jeong-Yeon Lim et al "Tyrosinase inhibitory p-coumaric acid from Ginseng leaves" Phytotherapy Research; 0951-418X, vol. 13 (1999), 5, p. 371-375.
Bombardelli E et al. Serenoa repens (Bartram) JK Small. Fitoterapia 1997; LXVIII (2):99-113.
Gupta, Senior Advisor and Director, TKDL, Observations by a third party filed with EPO by the Council of Scientific & Industrial Research, Dated May 18, 2010, 29 pages, European Patent Office.

* cited by examiner

*Primary Examiner* — Terry A McKelvey
*Assistant Examiner* — Catheryne Chen
(74) *Attorney, Agent, or Firm* — Davis & Bujold PLLC; Michael J. Bujold

(57) ABSTRACT

The present invention relates to selected and stabilized cell line extracts from *Ajuga reptans* comprising phenylpropanoids having high antioxidating capacity with a teupolioside titer of between 20% and 90% and a chromophore-free fraction of between 80% and 10%. Said extracts are for use in human and veterinary therapy and for nutritional and cosmetic purposes. Furthermore, the invention relates to a novel phenylpropanoid molecule denominated isoteupolioside.

14 Claims, 1 Drawing Sheet

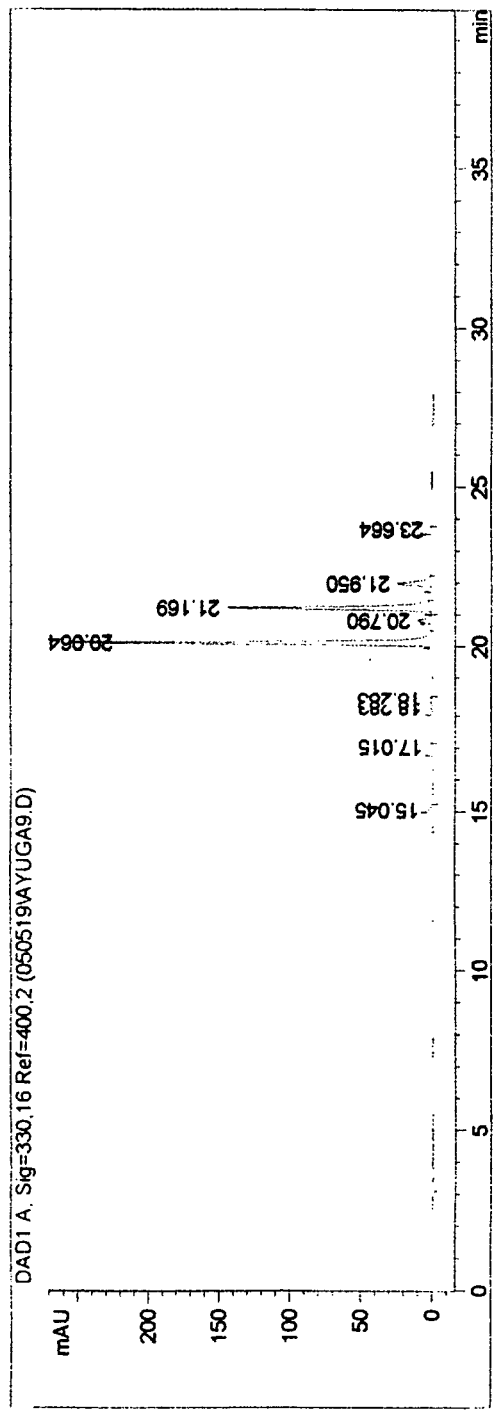

EXTRACTS FROM *AJUGA REPTANS* CELL LINES, THEIR PREPARATION AND USE

FIELD OF THE INVENTION

The present invention relates to extracts derived from *Ajuga reptans* plant cell cultures obtained in a fermenter. Particularly, the present invention concerns the preparation and use of said extracts, for the production of drugs or nutritional or cosmetic substances, said extracts possessing not only antioxidant activity but also other important pharmacological properties.

BACKGROUND OF THE INVENTION

Numerous studies have confirmed that oxidative stress is a phenomenon which progresses over time, causing biological damage leading to cell death, and which is responsible for both the effects connected with lipoprotein peroxidation and death due to degeneration, in addition to death due to apoptosis. Indeed, oxidative stress has been recognised as a mediator of programmed cell death, responsible for the activation of T lymphocytes and the depletion of CD4+ T cells in AIDS (Buttke T. M., Sandstrom P. A. "Oxidative stress as a mediator of apoptosis" Immunology Today, 1994, 15(1):7-10).

The antioxidant action of phenylpropanoids has been amply described and is well known in the literature (Seidel et al. Phenylpropanoids from *Ballota nigra* L. inhibit in vitro LDL peroxidation. Phytother. Res., 2000, 14(2): 93-98; Chion et al. Acteoside protects endothelial cells against free radical-induced oxidative stress. J. Pharm. Pharmacol., 2004, 56 (6): 743-8; Lee et al. Protective effect of acteoside on carbon tetrachloride induced hepatotoxicity. Life Sci., 2004, 74 (8): 1051-64), but sources for the large scale production thereof are completely absent, due to the very low quantities typically present in plant tissues and the high costs associated with the purification process.

SUMMARY OF THE INVENTION

Accordingly, a first object of the invention is a process for manufacturing extracts from *Ajuga reptans* cells, which allows to obtain industrial amounts of phenylpropanoids.

A second object of the invention is total extracts or single substances from plant cell lines that can be obtained according to the above process.

A third object is to provide pharmaceutical, cosmetic or nutritional uses, either for human, veterinary and zootechnical purposes, of said total extracts or single substances.

Further characteristics and the advantages of the present invention will be clearly understood from the following detailed description of the invention.

DETAILED DESCRIPTION OF THE INVENTION

The process of the invention comprises a first stage of cell culture selection based on the metabolite of interest.

Briefly, this process envisages the collection of plant tissue, the cleaning thereof, for example under running water, cutting into fragments of 2-5 cm and sterilisation on plates, for example by sequential treatment with 70% ethanol for approx. 15 minutes, 2% sodium hypochlorite for approx. 5 minutes and finally 0.05% $HgCl_2$ for approx. 1 minute. Between treatments, the plant fragments are washed, typically three or more times with sterile distilled water.

Each fragment of said tissue, chopped-up even further (explants), is placed on a Petri dish containing nutrient medium, solidified by the addition of Agar and supplemented with growth hormones without the addition of any antibiotics. The number of explants performed influences the outcome of the subsequent stages. Generally from 2000 to 5000 uncontaminated explants are sufficient to proceed to the subsequent selection stage.

Following a suitable period of time, undifferentiated callus tissue forms, which is then multiplied following transfer onto a greater surface area with fresh medium.

Preferably, the plant cell line derived from the undifferentiated callus tissue is preferably stabilised by means of a certain number of transfers (sub-cultures) onto fresh culture medium. Particularly, it has been observed that in order to obtain a stable cell line, it is important to perform at least ten sub-cultures. Such medium is solid in nature, and may be advantageously constituted by 0.8-1% agar in a standard culture medium, to which has been added plant peptone, allowing a balanced supply of aminoacids and guaranteeing the maintenance of good cell wall integrity. Preferably, plant peptone will be added in quantities ranging between 500 and 4000 mg/l of culture medium.

A "stable cell line" is defined as a culture having the following characteristics:
- high and constant proliferation rate over time;
- preservation of the same phenotypic characteristics throughout various subcultures (cell color, aggregate friability, size etc.);
- constant secondary metabolite levels per unit of mass, over the course of the various subculture steps (secondary metabolite content is assessed by chemical analysis of the extracts);
- constant primary metabolite content (protein, lipids and polysaccharides) per unit mass.

Subsequently, at the stabilisation stage, the cell line is subjected to "clonal selection". Such selection consists of growing the stabilised cells for an appropriate amount of time (typically, 10-15 days of culture). Subsequently, individual cell aggregates are taken from the solid culture medium and each of said cell aggregates is inoculated into liquid culture medium described above.

Following fermentation for such time necessary to obtain adequate multiplication of the cell aggregate (hereinafter referred to as "clone"), a time generally comprised of between 10 and 15 days, the content of the metabolite of interest is determined for each clone.

Such operations may be repeated until a plant cell line clone is selected, in which production of the metabolite of interest is the highest.

It should be remembered that alternating periods of culture on solid and liquid media is essential for the clonal selection process of the present invention. Hence, it is essential that the clonal selection process described above does not conclude with the identification of the most active clone, but is constantly repeated so as to keep the selected clone phenotypically homogeneous.

The selected plant cell line is then multiplied in order to obtain a sufficient quantity of biomass to carry out the production fermentation stage. Said quantity will depend on the specific production requirements, the plant cell line typology used and the type of metabolite it is desired to produce.

The biomass thus obtained may be passed directly into the final fermenter, or can be subjected to one or more further growth stages in liquid medium, working with intermediate volumes.

Preferably, the process just illustrated includes the stages of:

a) cultivating a predetermined plant cell line, stabilised for a sufficient period of time to allow the multiplication of said cell line to give substantially distinct cell clusters, on solid medium;

b) removing said substantially distinct cell clusters from said solid medium and placing each of them in a separate liquid culture medium;

c) cultivating each of the said substantially distinct cell clusters in said liquid culture medium for a sufficient period of time to allow the multiplication of said cell clusters, and the analytical determination of the primary and/or secondary metabolites produced thereby;

d) performing a qualitative and quantitative determination of the primary and/or secondary metabolites produced by each of said cell clusters in said liquid culture medium;

e) selecting the cell cluster capable of producing the greatest quantity of said metabolite of interest;

f) repeating the process cycle according to stages a), b), c), d) and e) on said cell cluster, selected according to stage e), a sufficient number of times until the quantity of said metabolite of interest produced by the selected cell cluster, and by the cell clusters deriving from further selection cycles, is essentially constant.

In addition, the subsequent fermentation may preferably consist of the following stages:

A) the inoculation of said plant clone into liquid medium and the multiplication thereof for a sufficient period of time to obtain an increase in cellular mass of at least 300% of the weight thereof;

B) optionally, transfer of the suspension obtained from stage A) into fresh liquid culture medium and the multiplication thereof for a sufficient period of time to obtain an increase in cellular mass of at least 300% of the weight thereof;

C) optionally, the repetition of stage B) at least one additional time;

D) the transfer of the suspension obtained in stages A), B) or C) into fresh liquid culture medium in a fermenter to give a biomass, and conducting the fermentation under such conditions and for a sufficient period of time so as to obtain within said biomass, the production of said at least one metabolite of interest;

E) the separation of said at least one metabolite of interest from said biomass.

In accordance with one preferred embodiment, the fermentation will normally be performed at a temperature of between 15° C. and 35° C., typically around 25° C. and for a period of time normally between 7 and 40 days, preferably between 14 and 21 days. It is essential that the biomass be adequately aerated and that at the same time be kept stirred by means of stirring external to the fermenter. Indeed, it has been observed that plant biomass is comprised of cells having cell-walls that are poorly resistant to rupture. A stirrer submerged into the biomass acts mechanically on the cells and can easily cause the lysis thereof. However, it is necessary that the stirring, although delicate, be efficient, above all in the final fermentation stages when the biomass greatly increases in density. For the purposes of the present invention, particularly appropriate methods of stirring are orbital means of stirring. Such means of stirring preferably operate at 40-200 rpm, more preferably at around 120 rpm.

It is appropriate that the volume of the container (fermenter) in which the fermentation occurs be considerably greater than the volume of the biomass. Typically, the volume of the reactor will be from 50% to 200% greater than the biomass volume.

As already mentioned, efficient fermentation requires adequate oxygenation. Oxygenation is normally performed by using sterile air with a flow rate of 0.5-4 l/minute, more preferably 2-2.5 l/minute, for a volume of 10 liters of biomass. Alternatively, gas mixtures containing from 10% to 100% v/v of oxygen may be used.

As mentioned previously in relation to stirring, even oxygenation by means of over violent bubbling can cause rupturing of the cell walls. Hence it is necessary to ensure that oxygenation is performed delicately, for example by bubbling through appropriate diffusers. It will be preferable to use means of air or oxygen diffusion with nozzle delivery flow speeds comprised of between 10 m/min and 600 m/min, more preferably between 50 m/min and 350 m/min.

In addition, the shape of the fermentation chamber has significant importance. Indeed, it is recommended that it has a smooth and uniform surface, i.e. that there are no edges, corners or other parts which can cause the cell walls of the biomass rupture.

According to one particular embodiment of the present invention, additives increasing water oxygen solubility will be added to the biomass. Such additives will preferably be selected from those substances defined as "artificial blood", for example the perfluorinated hydrocarbons (PFC).

Particularly, to the purpose of the present invention, stabilized cell lines derived from *Ajuga reptans* have been selected for their ability to produce phenylpropanoids (FP) in suitable qualitative and quantitative amounts.

Subsequently, substances from said plant cell lines, selected in the aforesaid manner, have been extracted by means of the following procedure.

Morphological Characteristics of the Cell Line

The *Ajuga reptans* cell line denominated IRBN22 at DSMZ (Deutsche Sammlung von Mikroorganismen und Zellkulturen, Braunschweig, D): DSM 16451, accession date: 31 Mar. 2004) stabilized and selected in accordance with the above procedure is yellowish and opaque with brittle-looking cells.

Extraction Process of an Extract from Plant Cell Lines

The extraction process comprises the following stages in sequence:

a) subjecting the biomass, obtained in accordance with the selection process described previously, to an enzyme deactivation treatment;

b) homogenising the product obtained following step a);

c) separating the aqueous phase from the cell residues by means of gravity filtration, pressure filtration or centrifugation through a porous mesh, for example nylon, steel or cotton mesh etc., preferably having a porosity comprised of between 10 μm and 300 μm, more preferably between 50 μm and 150 μm;

d) performing an extraction of the aqueous phase obtained following step c) using hydrophobic interaction resin, preferably in batch;

e) recovering the absorbed substances (extract) from the resin by means of elution with ethanol, or a mixture of alcohols having up to 5 carbon atoms (preferably ethanol), in water in percentages varying from 30% up to just under 100% by volume.

According to one particular aspect of the invention, between steps a) and b) a biomass filtration step may be performed under the same conditions reported in step c), with the aim of recovering just the biomass itself without any fermenter culture medium.

In particular, cultures of the cell line IRB22 in suspension, obtained in accordance with the cited procedures, are harvested with ages comprised of between 7 and 21 days. The enzyme deactivation treatment occurs, for example, by means of thermal treatment. Particularly, said thermal treatment occurs by heating the biomass at a temperature comprised of between 50° C. and 15° C., preferably between 60° C. and 120° C., for a time of less than 5 minutes, so as to inactivate all enzymes. Preferably, the thermal treatment involves the use of steam. Then, the biomass is homogenized using an ultraturrax, as described above. The substances present in the clear aqueous phase that has been obtained subsequent to filtration or centrifugation of the homogenized biomass are batch extracted with hydrophobic interaction resin, preferably selected from polystyrene-divinylbenzene or acrylic matrix resins, and the adsorbed products are recovered from the resin by means of one or more elution steps with aqueous ethanol, from 30% to 95% by volume.

In accordance with one particular embodiment, the entire biomass is filtered as described above, and subjected to thermal treatment with steam at 120° C. for a period of time varying between 5 and 30 minutes.

It should be noted that by "extract" is meant herein an extract derived from cell cultures of the plant *Ajuga reptans* (Labiatae family), deriving from any method comprising varying percentages by weight of phenylpropanoids, teupolioside, metilteupolioside e isoteupolioside, the latter being a chemical entity unknown in the prior art, and a fraction devoid of any characteristic chromophores, present in variable quantities depending on the preparation method and consisting mainly, but not exclusively, of oligo- and polysaccharide, protein and lipid molecules.

The extracts comprise phenylpropanoids of the following general formula (I), titrated in teupolioside

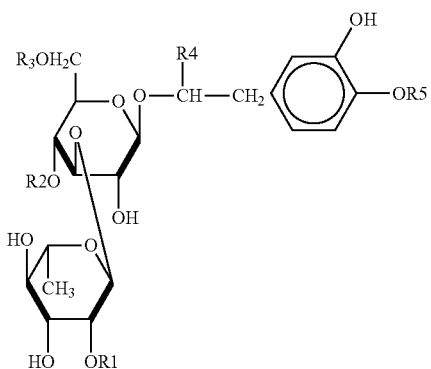

wherein:
R1 is a hydrogen atom or a monosaccharide with 5 or 6 carbon atoms or a disaccharide with 10 to 12 carbon atoms;
R2 is a hydrogen atom or is a caffeoyl (A) or feruloyl (B) group;
R3 is a hydrogen atom or a monosaccharide with 5 or 6 carbon atoms or a disaccharide with 10 to 12 carbon atoms or is a caffeoyl (A) or feruloyl (B) group;
R4 is a hydrogen atom, or a linear or branched alkyl group with 1 to 3 carbon atoms and preferably with 1 carbon atom or a hydroxyl;
R5 is a hydrogen atom, or a linear or branched alkyl group with 1 to 3 carbon atoms and preferably with 1 carbon atom;
With the proviso that, when R3 is a caffeoyl (A) or feruloyl (B) group,

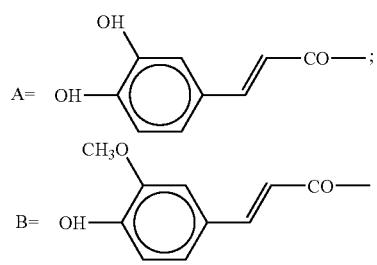

then R2 is always a hydrogen atom and vice versa. R4 and R5 can be either the same or different.

Extraction occurs by bringing the clear solution obtained subsequent to filtration or centrifugation of the homogenized biomass into contact with an appropriate quantity of resin, separating the resin and eluting said resin with a suitable eluent.

The attainment of the extracts varies as a function of numerous parameters. The use of fermentation supernatant (which contains the part of the fraction devoid of chromophores and which is released from the cells during culture) during the filtration stage leads to a slight enrichment in phenylpropanoids due to the dilution effect. A second factor is the quantity of resin used in relation to the quantity of material to be extracted, with less resin promoting the selective attachment of phenylpropanoids and hence consequent enrichment of the eluate. Furthermore, different enrichments may be obtained depending on the $EtOH/H_2O$ ratios used to recover the compounds absorbed onto the resin, since lesser percentages of ethanol in the eluent predominantly extract the fraction devoid of chromophore, while subsequent elution with a mixture containing a higher percentage of ethanol leads to the preferential extraction of phenylpropanoids.

Thus it is possible to obtain extracts containing from 20% to 90% phenylpropanoids by weight, preferably between 30% and 60%, with the remaining percentage fraction, comprised of between 80 and 10%, preferably between 70% and 40%, being comprised of a chromophore-free fraction, comprising mainly, but not exclusively, oligo- and polysaccharide, protein and lipid type molecules.

It has also been surprisingly found that the thermal treatment performed on the biomass causes the isomerisation of teupolioside to isoteupolioside, and that the extent of said isomerisation depends on the treatment temperature and time. Temperatures comprised of between 50° C. and 150° C., preferably between 60° C. and 120° C., for a period of time sufficient to cause isomerisation (measurable by HPLC analysis as reported previously), preferably between 5 and 30 minutes, are generally used to obtain the transformation of a percentage ranging between 40% and 60% of the teupolioside initially present into isoteupolioside. Thereby, the content of such substances in the filtered clear solution will also be modified. The thermal treatment may be performed by heating externally or internally for example by the insufflation of steam into the biomass.

Non-thermally treated biomass will generally contain a percentage of between 5% and 25% isoteupolioside with respect to the mass of phenylpropanoids. Following thermal treatment, the percentage of isoteupolioside will generally be comprised of between 30% and 65% of the total mass of phenylpropanoids.

The above described isomerisation may occur in all those phenylpropanoids of general formula I wherein R3 is a hydrogen atom and R2 is other than hydrogen.

Accordingly, a process for the isomerisation of phenylpropanoids of general formula I, wherein R3 is a hydrogen atom and R2 is anything other than hydrogen, comprising a thermal treatment stage of said phenylpropanoids as described above, constitutes a further subject of the present invention.

A particular compound defined above as FPD has been identified among the phenylpropanoids that can be obtained by means of said processes. This novel compound, denominated isoteupolioside, has proved effective as an anti-oxidant in an analogous manner to teupolioside. Furthermore, other important pharmacological, cosmetic and nutritional properties have been observed, such as described below.

It has been also surprisingly found that the action of the individual phenylpropanoids, as well as any mixture thereof, is considerably increased, in some cases, when plant cell extracts are associated with said chromophore-free fraction. Thus, it is clear that an unexpected synergic effect is created, for particular activities, between the phenylpropanoids and the chromophore-free fraction which enhances the action of the phenylpropanoids.

In other cases, teupolioside and isoteupolioside have been found to exhibit pharmacological activities comparable to the inventive extracts. Particularly, the teupolioside and isoteupolioside have a platelet aggregation, anti-inflammatory and anti-lipoxygenase, anti-5alpha reductase, anti-tyrosinase, antifungal and metal-chelating ($Fe^{2+}$, $Fe^{3+}$, $Cu^{2+}$ e $Ni^{2+}$) activity.

Several processes are reported by way of non-limiting example.

EXAMPLE 1

Calluses grown on solid medium (GAMBORG B5 in 1% agar supplemented with 20 g/l sucrose, 2 g/l plant peptone, 1 mg/l kinetin, 1 mg/l naphthalenacetic acid, 0.2 mg/l indolacetic acid at pH 6.5) and subjected to subculture for at least three months, are inoculated into 20×300 ml flasks, each containing 50 ml of liquid medium (GAMBORG B5 supplemented with 20 g/l sucrose, 2 g/l plant peptone, 1 mg/l kinetin, 1 mg/l naphthalenacetic acid, 0.2 mg/l indolacetic acid at pH 6.5). Following fermentation for 7 days, the cultures are used to likewise inoculate 1000 ml flasks, each containing 250 ml of liquid medium which are then unloaded after a period 14 days. The biomass is combined and filtered through nylon mesh with a porosity of 100 μm. The cells are suspended in an equal volume of $H_2O$ and briefly treated with steam (3-4 minutes). The suspension is then homogenised using an ultraturrax and centrifuged in order to remove the sold residue. The latter is then taken up in 5 vol. of $H_2O$ then homogenised and centrifuged. The supernatants are combined and titrated by HPLC.

The analysis shows a content of phenylpropanoid expressed as teupolioside equal to 18.6 g. To the aqueous solution is added 2 kg of Diaion HP 2MG resin and the slurry left stirring overnight. After removal of the aqueous phase by filtration, the resin is washed with a first portion of 10 liters of hydroalcoholic mixture $EtOH:H_2O$ (20:80), then eluted with three 10 liter batches of $EtOH:H_2O$ mixture (80:20). The combined eluates are concentrated to a small volume in an evaporator under reduced pressure. The lyophilised residual aqueous phase yields 14.5 g of a yellow powder. Typically, the extract thus obtained (Extract 1) has a titre equal to approx. 90% in phenylpropanoids (13.06 g) expressed as teupolioside, and approx. 10 wt %, in other components, constituted mainly, but not exclusively, by oligo- and polysaccharides, protein and lipid (saccharide fraction) type molecules.

EXAMPLE 2

40×1000 ml flasks, each containing 250 ml of culture obtained from calluses grown on solid medium (GAMBORG B5 in 1% agar supplemented with 20 g/l sucrose, 2 g/l plant peptone, 1 mg/l kinetin, 1 mg/l naphthalenacetic acid, 0.2 mg/l indolacetic acid at pH 6.5) following 14 days of fermentation are used to similarly inoculate 3 liter flasks, each containing 1 liter of liquid medium (GAMBORG B5 supplemented with 20 g/l sucrose, 2 g/l plant peptone, 1 mg/l kinetin, 1 mg/l naphthalenacetic acid, 0.2 mg/l indolacetic acid at pH 6.5). After a further 14 days of fermentation, these are in turn used to inoculate 10 30 liter fermenters, each containing 20 liters of liquid medium. After a further 14 days, the fermenters are in turn used as the inoculum (equal to 250 liters) for a fermenter with a capacity of 1000 liters, containing 600 liters of medium. Fermentation is monitored by means of samples taken sequentially over time and, is terminated upon reaching an age of 20 days. Final production is equal to 2.4 g/l, for a total of 2040 g of phenylpropanoids expressed as teupolioside (600 liters+250 liters of inoculum). Steam at 120° C. is insufflated into the reactor for 20 minutes, then the biomass is unloaded therefrom, homogenised and filtered. To the aqueous phase is then added 150 kg of Diaion HP 2MG resin and this is then left stirring overnight. At the end of said period, the resin is allowed to settle into a column with a diameter of 50 cm and height of 150 cm. The spent aqueous phase is left to slowly flow out from the bottom of the column, which is then washed with copious amounts of water (500 liters), then firstly eluted with 200 liters of hydroalcoholic mixture $EtOH:H_2O$ (20:80), then with 500 liters of $EtOH:H_2O$ mixture (80:20), at a flow rate of 300 ml/min. The eluate is concentrated under reduced pressure to give an aqueous residue which is then lyophilised. 3778 g of lyophilisate are obtained. Typically, the extract thus obtained (Extract 2) is constituted by approx. 54 wt % of phenylpropanoids expressed as teupolioside, and approx. 46% of other components, constituted mainly, but not exclusively, by oligo- and polysaccharides, protein and lipid (chromophore-free fraction) type molecules.

EXAMPLE 3

From HPLC analysis of the crude product obtained in example 2, teupolioside and its analogue metilteupolioside and a new phenylpropanoid denominated the isoteupolioside are the main components belonging to the class of caffeic derivatives, and are typically accompanied by less abundant products belonging to the same class.

With the aim of purifying the compounds of interest, in order to assess their activities, chromatographic purification using a 7×150 cm column, packed with Sephadex LH20 resin and equilibrated in 8% EtOH in water was used. The column was loaded with 90 g of extract obtained from example 2 and eluted isocratically using the same solvent. All the fractions were analysed by HPLC using the method described below and those containing the same products combined, concentrated and lyophilised. In particular, three groups of fractions have been identified containing the pure molecules, teupolioside (22.8 g) metilteupoliside (0.80 g) and isoteupolioside (12.75 g).

High pressure liquid chromatography (HPLC) analysis is performed using a Phenomenex 4.6×150 mm C18 (2) column. Phase A—water/0.01 N phosphoric acid; Phase B—acetonitrile/0.01 N phosphoric acid; flow rate—0.8 ml/min. Gradient:

| Time | % B |
| --- | --- |
| 0 | 0 |
| 10 | 10 |
| 15 | 20 |
| 20 | 25 |
| 25 | 35 |
| 30 | 45 |
| 35 | 55 |
| 40 | 0 |

The retention times of the 3 phenylpropanoids present in the extracts are reported in table 1.

TABLE 1

Retention times of the phenylpropanoids coded as A, B, D.

| Phenylpropanoid | FPA | FPB | FPD |
| --- | --- | --- | --- |
| RT* | 19.9–20.2 | 21.8–22.1 | 21.0–21.3 |

*Retention time in minutes (interval)

The structure of the phenylpropanoids has been confirmed by means of mass spectrometry (MS) and nuclear magnetic resonance (NMR) and reported in the Table 2 below. Table 2.

TABLE 2

| Substituents | FPA | FPB | FPD |
| --- | --- | --- | --- |
| R1 | Galactose | Galactose | Galactose |
| R2 | Caffeic ac. | Ferulic ac. | H |
| R3 | H | H | Caffeic ac. |

The phenylpropanoid coded as FPA corresponds to the structure already known as teupolioside, FPB is b-(3,4-dihydroxyphenyl)ethyl-O-a-L-ramnopyranosyl (1″-3′)-O-b-D-galactopyranosyl(1‴-2″)-b-D-(4′-O-trans-feruloyl)glucopyranoside already previously described (EP1118617) and more simply defined as metilteupolioside. Antioxidant activity has been described for these two phenylpropanoids. On the other hand, the phenylpropanoid coded as FPD has not been described in the literature so far. FIG. 1 reports the HPLC analysis of a composition, by way of example.

Table 3 below reports the percentage concentration of each component of the Extract 1 and Extract 2.

TABLE 3

Qualitative and quantitative determination of the phenylpropanoids present in the Extracts 1 and 2 expressed by total weight percentage and calculated as teupolioside.

| | (wt %) concentration of each fraction | | | |
| --- | --- | --- | --- | --- |
| Phenylpropanoid | FPA | FPB | FPD | Chromophore-free fraction |
| Extract 1 | 73.6 | 7.1 | 9.7 | 9.6 |
| Extract 2 | 33.9 | 1.2 | 18.9 | 46 |

Several examples, which are given by way of non-limiting illustration, of the pharmacological antioxidant, anti-inflammatory, metal-chelating, platelet aggregation-disaggregation, anti-5alpha reductase, anti-lipoxygenase, anti-tyrosinase and antimicrobial activity of the inventive Extracts, teupolioside and isoteupolioside are set forth herein below.

EXAMPLE 4

Antioxidant Activity of the *Ajuga Reptans* Extracts, and Isoteupolioside by Means of Biochemical Assays Based on Chemiluminescence Measurements

*Ajuga reptans* Extracts 1 and 2, prepared as described in examples 1 and 2, and isoteupolioside have been used to assess in vitro antioxidant action with specific oxygen radical generating systems such as the superoxide anion ($O_2^-$), the hydroxyl radical ($HO^-$), the peroxynitrite radical ($ONOO^-$) and the inhibition of lipid peroxidation. The superoxide anion has been measured by a chemiluminescent assay based on the hypoxanthine (HPX)/xanthine oxidase (XOD) reaction using the Lumimax Superoxide Anion Detection Kit (Stratagene, La Jolla, Calif., USA) and following the manufacturer's instructions. Hydroxyl radical scavenger activity has been measured by means of the Fenton reaction for the production of hydroxyl radicals and chemiluminescent dosage (using a Victor$^3$ chemiluminometer, Wallac, Finland) with luminol. Peroxynitrite ions have been determined by means of dosage with a spontaneous generator of peroxynitrites (3-morpholinosidnonimine hydrochloride; SIN-1) and a stable reagent for the nitroxyl ions (2-(4-carboxyphenyl)-4,4,5,5-tetramethylimidazoline-1-oxyl-3-oxide potassium salt PTIO spin trap) then dosed by means of electron spin resonance (ESR) using a Nippon Denshi JES-FR30. Lipid peroxidation has been generated using $Fe^{2+}$ induced-oxygen reactive species, and detected using thiobarbituric acid in accordance with Buege, J A & Aust, S D: Microsomal lipid peroxidation (Methods Enzymol.

TABLE 4

Effects of the Ajuga reptans Extracts, teupolioside, isoteupolioside, rutin and aloin on various assays of antioxidant activity (expressed as $IC_{50}$)

| | Superoxide radical | Hydroxyl radial | Peroxynitrite radical | Lipid peroxidation |
| --- | --- | --- | --- | --- |
| Extract 1 | 0.17 µg/ml | 0.51 µg/ml | 1.6 µg/ml | 7.8 µg/ml |
| Extract 2 | 0.17 µg/ml | 0.45 µg/ml | 1.3 µg/ml | 8.8 µg/ml |
| Teupolioside | 1 µg/ml | 1.6 µg/ml | 1.8 µg/ml | 9.4 µg/ml |
| Iso-teupolioside | Not determined | 1.04 µg/ml | Not determined | 9.14 µg/ml |
| Rutin | 10 µg/ml | 3.9 µg/ml | 10 µg/ml | Not determined |
| Aloin | 7.6 µg/ml | 2.9 µg/ml | 12.3 µg/ml | Not determined |

The Extract 1 and the Extract 2 set forth in Table 4 are derived from *Ajuga reptans* cell cultures comprising the phenylpropanoids at 90% and 54%, respectively. The results are expressed as the concentration inhibiting 50% of activity ($IC_{50}$), means of 6 independent assays.

The assayed *Ajuga reptans* extracts have shown themselves to be extremely effective scavengers of oxygen free radicals, independently of their degree of purity. For the superoxide, hydroxyl and peroxynitrite radicals, both Extract 1, and Extract 2 possess greater capacity with respect to the classic flavonoids, such as for example rutin and aloin. In the superoxide and peroxynitrite generation assay, the $IC_{50}$ for rutin and aloin is 10 μg/ml, 7.6 μg/ml and 12.3 μg/ml, respectively, concentrations approximately 6 to 30 fold higher with respect to *Ajuga reptans* Extract 1 and Extract 2. The $IC_{50}$ for rutin and aloin for the inhibition of the production of hydroxyl radicals is 3.9 μg/ml and 2.9 μg/ml respectively, from 5 to 7 times higher with respect to the value determined for the *Ajuga reptans* Extracts. The Extracts have also shown themselves to be extremely effective in reducing iron ion-induced lipid peroxidation. The antioxidant activity of pure teupolioside is surprisingly less effective in comparison to *Ajuga reptans* Extracts 1 and 2 in activity assays against superoxide and hydroxyl radicals and, even though only slightly, in the inhibition of lipid peroxidase. This tends to indicate higher antioxidant activity in the Extracts with respect to pure teupolioside. Isoteupolioside has proved a little more effective than teupolioside, and however a little less effective than Extracts 1 and 2.

EXAMPLE 5

Anti-Inflammatory Activity of *Ajuga Reptans* Extracts, Teupolioside and Isoteupolioside on Whole Blood and White Blood Cells Anti-inflammatory activity has been assessed by measuring luminol dependent chemiluminescence generated by free radicals released from whole blood and from white blood cells. The assay has been performed using the following protocol: 10 μl of fresh human blood is mixed with 0.980 ml of Hanks saline solution containing $5 \times 10^{-5}$ M luminol and the test sample (at various concentrations). The chemiluminescent response is recorded continuously for 30 minutes at a temperature of 37° C. The results are expressed as $IC_{50}$ (mg/ml), i.e. as the minimum sample concentration inhibiting chemiluminescence by 50% with respect to the control. To isolate white blood cells (WBC) from whole blood one proceeds in the following manner: 1 ml of fresh blood is layered onto a Hipaque gradient (p=1.119) and centrifuged at 250×g for 60 minutes at room temperature. Following centrifugation, the pellet containing the white blood cells is washed twice, using a large volume of cold Hanks saline solution. Finally, the washed WBCs are resuspended in 0.1 ml di HBSS containing foetal calf serum. $10^6$ WBC are added to a chemiluminometer cuvette. 10 μl of PMA (final concentration equal to 10 nM) are added to induce the formation of free radicals. The chemiluminescent response is recorded continuously for 30 minutes at a temperature of 37° C. The results are expressed as $IC_{50}$ (mg/ml), i.e. as the minimum sample concentration inhibiting chemiluminescence by 50% with respect to the control.

These determinations have been carried out on the *Ajuga reptans* Extracts 1 and 2, teupolioside and isoteupolioside.

Table 5 reports the values obtained for the these determinations.

TABLE NO. 5 anti-inflammatory activity of Ajuga reptans extracts, teupolioside and isoteupolioside on whole blood and white blood cells.

|  | Whole blood chemiluminescence (IC50 mg/ml) | White blood cell chemiluminescence (IC50 mg/ml) |
|---|---|---|
| Extract 1 | 0.57 | 0.05 |
| Extract 2 | 1 | 0.2 |

TABLE NO. 5-continued anti-inflammatory activity of Ajuga reptans extracts, teupolioside and isoteupolioside on whole blood and white blood cells.

|  | Whole blood chemiluminescence (IC50 mg/ml) | White blood cell chemiluminescence (IC50 mg/ml) |
|---|---|---|
| Isoteupolioside | 1.3 | 0.4 |
| Teupolioside | 1.4 | 0.5 |

The inhibition of the production of free radicals released by the white blood cells is correlated with the anti-inflammatory activity of the substance assayed. The Extracts 1 and 2 of *Ajuga reptans* have proved to be effective inhibitors of the production of free radicals both from whole blood and white blood cells. The inhibitory capacity shown by the extracts is greater than that of pure teupolioside and isoteupolioside.

EXAMPLE 6

The Platelet Anti-Aggregating and Disaggregating Activities of *Ajuga Reptans* Extracts, Teupolioside and Isoteupolioside Platelet enriched rabbit plasma has been used to assess the platelet anti-aggregating and disaggregating properties of *Ajuga reptans* Extracts compared with teupolioside and isoteupolioside. Platelet rich plasma has been obtained from rabbit venous blood by mixing it with a 3.8% sodium citrate solution (9:1 v/v). The solution has then been centrifuged at 460×g for 20 minutes. The supernatant has been collected and immediately used for the aggregation assays. Platelet aggregation has been recorded using a Chronolog "Ionised calcium platelet aggregometer" (Chrono-log Co., USA). All measurements have been performed at 37° C. with continuous stirring. One milliliter of the platelet suspension (in the presence or absence of the test substances) has been added to the cuvettes and incubated for five minutes to equilibrate the cells to 37° C. Then 10 μl of a solution of ADP (final concentration—10 μM) has been added and the luminous transmittance continuously recorded. The results are expressed as the DT/DTK ratio, where DTK and DT are the luminous transmittance values, in the absence and presence of extract respectively.

Platelet disaggregation (the disappearance of pre-formed aggregates) has been determined using the same luminous transmittance curve 10 minutes following the addition of ADP. The results are expressed as the DR/DRk ratio, where DRk and DR, are the luminous transmittance in the absence and presence of extract. The test substances, diluted in physiological solution (isotonic saline) (pH 7.4) are pre-incubated with the platelet rich plasma (1:10 v/v) for 5-40 minutes. The aggregation measurements have then been performed. Physiological solution carrier has been added to the control samples (1:10 v/v). The values are set forth in Table 6 and Table 7.

TABLE 6

The effect of Extract 2 on ADP induced platelet aggregation-disaggregation

| Extract 2 mg/ml | Control aggregation | Control disaggregation | Latency period |
|---|---|---|---|
| 0.001 | 105 ± 5 | 125 ± 8 | 74 ± 16 |
| 0.01 | 99 ± 11 | 150 ± 8[#] | 78 ± 5[#] |

TABLE 6-continued

The effect of Extract 2 on ADP induced platelet aggregation-disaggregation

| Extract 2 mg/ml | Control aggregation | Control disaggregation | Latency period |
|---|---|---|---|
| 0.1 | 102 ± 8 | 174 ± 8## | 78 ± 8# |
| 1.0 | 90 ± 10 | 163 ± 19## | 73 ± 6# |

"- Mean ± SD (n = 6);
p < 0.05 vs. control
p < 0.01 vs. control

TABLE 7

The effect of teupolioside on ADP induced platelet aggregation-disaggregation

| Teupolioside mg/ml | Control aggregation | Control disaggregation | Latency period |
|---|---|---|---|
| 0.001 | 121 ± 6 | 105 ± 5# | 101 ± 3 |
| 0.01 | 110 ± 10 | 113 ± 10# | 95 ± 5# |
| 0.1 | 114 ± 10 | 124 ± 15## | 94 ± 4# |
| 1.0 | 68 ± 9 | 100 ± 10## | 66 ± 10# |

"- Mean ± SD (n = 6);
p < 0.05 vs. control
p < 0.01 vs. control

In the platelet disaggregation test, the isoteupolioside exhibited an activity similar to teupolioside.

The Extract 2 produces a very significant increase in the platelet disaggregating action at concentrations ranging between 0.01 mg/ml and 1 mg/ml. The disappearance of small platelet aggregates is 1.5 fold greater than the control, while no significant anti-aggregating effects are evident on the platelet preparation. Furthermore, the latency time for the beginning of the disaggregation step is significantly reduced from 5.3 minutes on average (control) to 3.7 minutes on average (Extract 2). The teupolioside produces a modest inhibiting effect on platelet aggregation, only at 1 mg/ml concentration, whereas the extracts are not effective in preventing the platelet aggregation.

EXAMPLE 7

The Fe2+, Fe3+, Cu2+ and Ni2+ Metal Chalating Action of *Ajuga Reptans* Extracts, Teupolioside and Isoteupolioside The chelating activities of *Ajuga reptans* extracts in relation to $Fe^{2+}$, $Fe^{3+}$, $Cu^{2+}$ and $Ni^{2+}$ metal ions has been determined by means of spectrophotometric measurements using a Shimadzu 1770 UV spectrophotometer. The activities of chelating agents depends on the association constant (equilibrium) of their reactions with the metals according to the following reaction [1]:

$$K_{eq} \quad [1]$$

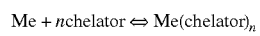

$$Me + n\text{chelator} \Leftrightarrow Me(\text{chelator})_n$$

wherein $K_{eq}$ is the equilibrium constant equal to the ratio of concentrations at equilibrium of a complex and a product of equilibrium concentrations of metal ions and a chelator:

$$K_{eq} = \frac{[Me(\text{chelator})_n]}{[Me][\text{chelator}]^n} \quad [2]$$

The method used for determining chelating activities is well documented in the literature (Korkina L G, Afarras'er I B. Antioxidant and chelating properties of flavonoids. Adv. Pharmacol., 1997, 38:151-63). The results are expressed as Keq ($M^{-1}$) calculated for a pure phenylpropanoid. This way the chelating activity against ferrous (Fe II), ferric (Fe III), copper (Cu II) and nickel ions has been calculated.

TABLE 8

Chelation equilibrium constants (Keq, $M^{-1}$) for the Ajuga reptans extracts, teupolioside and isoteupolioside.

| Samples | $Fe^{2+}$ (Keq, $M^{-1}$) | $Fe^{3+}$ (Keq, $M^{-1}$) | $Cu^{2+}$ (Keq, $M^{-1}$) | $Ni^{2+}$ (Keq, $M^{-1}$) |
|---|---|---|---|---|
| Extract 1 | $0.37 \times 10^6 \pm 0.001 \times 10^6$ | $0.46 \times 10^6 \pm 0.10 \times 10^6$ | $0.09 \times 10^6 \pm 0.02 \times 10^6$ | 2749-??-? 402 |
| Extract 2 | $0.49 \times 10^6 \pm 0.13 \times 10^6$ | $0.16 \times 10^6 \pm 0.06 \times 10^6$ | $0.11 \times 10^6 \pm 0.03 \times 10^6$ | 2040-??-? 752 |
| Teupolioside | $0.35 \times 10^6 \pm 0.02 \times 10^6$ | $0.43 \times 10^6 \pm 0.09 \times 10^6$ | $0.08 \times 10^6 \pm 0.03 \times 10^6$ | 2658 ± 365 |
| Isoteupolioside | $0.34 \times 10^6 \pm 0.01 \times 10^6$ | $0.42 \times 10^6 \pm 0.11 \times 10^6$ | $0.07 \times 10^6 \pm 0.02 \times 10^6$ | 2631 ± 373 |
| Rutin | $0.14 \times 10^6 \pm 0.04 \times 10^6$ | $0.16 \times 10^6 \pm 0.04 \times 10^6$ | $0.11 \times 10^6 \pm 0.04 \times 10^6$ | 635 ± 169 |

The chelating activity of the Extracts 1 and 2 from *Ajuga reptans*, teupolioside and isoteupolioside in relation to Fe2+ and Ni2+ metal ions, is about 3-4 fold higher than the rutin reference molecule.

EXAMPLE 8

Anti 5 Alpha Reductase and Anti-Lipoxygenase Activities of the *Ajuga Reptans* Extracts, Teupolioside and Isoteupolioside Useful for the Treatment of Juvenile Acne and the Prevention of Hair Loss Juvenile acne shows a multifactorial aetiology; one factor which plays a fundamental role is the following: during puberty and adolescence, there is increased production of the hormone testosterone. In the skin, this hormone is converted by the enzyme 5 alpha reductase into the hormone dihydrotestosterone, the latter causes enlargement of the sebaceous glands with a concomitant increase in sebum secretion. High levels of the enzyme 5 alpha reductase is also one of the major causes of hair loss (Thiboutot D., Harris G., Iles V., Cimis G., Gillilaud K., Hagari S. Activity of the type 1.5 alpha reductase exhibits regional differences in isolated sebaceous glands and whole skin. J. Invest. Dermatol. 1995; 105:209-14).

Data reported in the bibliography, show that extracts derived from the plant *Serenoa repens*, have anti-hair loss activity in that they possess inhibitory activities in relation to two enzymes: 5-alpha reductase and lipoxygenase (*Serenoa repens* (Bartram) J. K. Small. Fitoterapia 1997; LXVIII (2):99-113).

Determination of the 5 alpha reductase inhibitory activities by *Ajuga reptans* extracts in comparison to *Serenoa repens* extracts. Said determination has been performed using enzymes (5 alpha reductase, type I and type II) produced by genetically modified yeast. Enzyme activities have been determined in the presence of *Ajuga reptans* extracts, teupolioside, isoteupolioside and *Serenoa repens* extracts.

Type I 5 alpha reductase activity has been assayed by incubating the enzyme in 0.1 M Tris-citrate buffer (pH 7.0), containing 5 μM [$^{14}$C] radio-labelled testosterone (Amersham, Sweden) and 5 mM NADPH (Sigma) in a final volume of 5 ml. The solution thus obtained has been incubated for 1 hour at 37° C.

Determination of the type II 5 alpha reductase activity has been performed in an analogous manner to that just described, with the exception of a different pH value for the 0.1 M Tris-citrate buffer (pH 5.0).

In both assays, the steroids have been extracted using 5 ml of methylene chloride. The extracts have then been dried under a stream of nitrogen and the dried residues obtained have been dissolved in 20 μl of a chloroform-methanol mixture (2:1 v/v). An aliquot of said mixture has been deposited on the surface of a silica gel TLC plate. The solvent mixture used to develop the TLC has been the sane used to solubilise the dried residues. At the end of the TLC run, following UV detection, the $R_f$ values of the metabolites have been compared with those of standard steroids, chromatographed simultaneously with the other samples. For quantification of the results, the spots have been scraped from the TLC plate and extracted with 2 ml of ethyl acetate. The extracts obtained have been analysed, using scintillation fluid, with the aid of a Wallach β-counter. The enzyme activity has been calculated from the percentage conversion (C %) of the substrate into final product:

C%=[counted product/(counted substrate+product)]×100.

The results are reported in the following Table 7. Determination of the inhibition of lipoxygenase activity The inhibition of lipoxygenase activity by *Ajuga reptans* extracts has been demonstrated using a method based on the measurement of chemiluminescence (Laakso S., Lilius E M, and Turunen P. Determination of cis-,cis-methylene interrupted polyunsaturated fatty acids in aqueous solutions by lipoxygenase chemiluminescence. J. Biochem. Biophys. Methods 1984; 9(1):61-68).

The results obtained are summarised in table 9.

TABLE 9

Inhibition of the enzymes 5 alpha reductase and lipoxygenase (expressed as $IC_{50}$) by Ajuga reptans extracts, Serenoa repens plant extracts, teupolioside and isoteupolioside.

| Samples assayed | Type II 5 alpha reductase inhibition (IC50) | Type II 5 alpha reductase inhibition (IC50) | Lipoxygenase inhibition (IC50) |
|---|---|---|---|
| Extract 1 | 16 μg/ml | 24 μg/ml | 13 μg/ml |
| Extract 2 | 11.2 μg/ml | 16.3 μg/ml | 12.5 μg/ml |
| Teupolioside | 17 μg/ml | 24 μg/ml | 14 μg/ml |
| Isoteupolioside | 16 μg/ml | 26 μg/ml | 14 μg/ml |
| Serenoa repens extract | 12 μg/ml | 44 μg/ml | 18.5 μg/ml |

*Ajuga reptans* Extracts 1 and 2, teupolioside and isoteupolioside have significant inhibitory capacity in relation to the enzymes 5 alpha reductase (type I and type II) and lipoxygenase. The inhibitory activity of the *Ajuga reptans* extracts, teupolioside and isoteupolioside is greater than that shown by *Serenoa repens* plant extracts, particularly in relation to type II 5-alpha reductase, which is the principal agent responsible for the onset of acne and androgenetic alopecia and is an important cause of prostate diseases.

EXAMPLE 9

Anti-Tyrosinase Activity of the *Ajuga Reptans* Extracts, Teupolioside and Isoteupolioside to be Used for Skin Bleaching The enzyme tyrosinase catalyses the reactions leading to melanin biosynthesis from tyrosine. L-atyrosine is oxidised to 3,4 dihydroxyphenylalanine (L-DOPA), through the action of the enzyme tyrosinase, and again by means of a reaction catalysed by the same enzyme, 3,4 dihydroxyphenylalanine is converted to DOPAquinone. Substances inhibiting tyrosinase activity produce a clearing/bleaching effect on the skin, since they block melanin synthesis. The method used to determine the inhibition of tyrosinase activity in the oxidation reaction of L-tyrosine to L-DOPA is that described in Kim et al. (4,4'-Dihydroxybiphenyl as a new potent tyrosinase inhibitor. Biol. Pharm. Bull. 28(2), 323-327, 2005). The method applied for determination of the inhibition of tyrosinase activity in the conversion of L-DOPA to DOPAquinone is that described in Masamoto et al. (Mushroom tyrosinase inhibitory activity of esculetin isolated from seeds of *Euphorbia lathyris* L. Biosci. Biotechnol. Biochem., 67(3), 631-634, 2003). The results obtained from the inhibition assay of tyrosinase activity by *Ajuga reptans* extracts, teupolioside and isoteupolioside in comparison to resorcinol and kojic acid, are summarised in tables 10 and 11.

TABLE 10

Percentage tyrosinase enzyme activity inhibition in the oxidation of L-tyrosine to L-DOPA, by *Ajuga reptans* extracts, teupolioside and isoteupolioside in comparison to resorcinol and kojic acid.

| Compound | concentration | Test L-tyrosine-DOPA inhibitory activity (%) |
|---|---|---|
| Resorcinol | 250 µg/ml | 56.9 |
| Kojic acid | 250 µg/ml | 94.1 |
| Extract 1 | 250 µg/ml | 25 |
| Extract 2 | 250 µg/ml | 19.3 |
| Teupolioside | 250 µg/ml | 29.6 |
| Isoteupolioside | 250 µg/ml | 30.9 |

As may be seen from the data summarised in table 10, the *Ajuga reptans* Extracts 1 and 2, isoteupolioside and teupolioside exert significant inhibitory activity towards the enzyme tyrosinase.

TABLE 11

Percentage tyrosinase enzyme activity inhibition in the conversion of L-DOPA to L-DOPAquinone, by *Ajuga reptans* extracts, teupolioside and isoteupolioside in comparison to resorcinol and kojic acid.

| Compound | concentration | Test LDOPA-DOPAquinone inhibitory activity (%) |
|---|---|---|
| Resorcinol | 100 µg/ml | 0 |
| Kojic acid | 100 µg/ml | 35 |
| Extract 1 | 100 µg/ml | 33.4 |
| Extract 2 | 100 µg/ml | 25.4 |
| Teupolioside | 100 µg/ml | 21 |
| Isoteupolioside | 100 µg/ml | 20 |

Table 11 highlights the high inhibitory capacity of Extracts 1 and 2, isoteupolioside and teupolioside towards the enzyme tyrosinase activity. The enzyme inhibitory activities of the *Ajuga reptans* extracts, teupolioside and isoteupolioside are higher with respect to those of the resorcinol reference molecule and similar to that of kojic acid.

EXAMPLE 10

Oxidative Stress on Human Endothelial Cell (A549) Cultures

The following abbreviations have been employed in the description:

| BSO | buthionine [S,R] sulphoximine |
|---|---|
| GSH | reduced glutathione |
| DCF | Dichlorofluorescein |
| FCS | foetal calf serum |
| MTT | 3-(4,5-dimethylthiazole)-2,5-diphenyl tetrazol bromide |

Materials and Methods
Test Model $10 \times 10^5$ A549 cells (ATCC-CCL185) have been seeded into wells with 3 ml of DMEM/F12K HAM medium (Sigma-Aldrich) with 10% FCS and incubated at 37° C. in a 5% $CO_2$, water vapour saturated atmosphere. After 24 hours the culture medium is replaced by medium supplemented with BSO, which is left in contact with the cells for 20 hours. The medium is once again replaced with medium containing BSO in the presence or absence of the test compound. After 4 hours, quantitative measurement of the ROSs (hydroxyl radicals) is performed by washing the cells with phosphate buffer and then incubating them with 30 µM DCF-DA in buffer solution. At the end of a 15 minute incubation, excess DCF-DA is removed from the cells by washing, prior to measuring the fluorescence emitted.

Parameters
Fluorimetry.

Antioxidant activity measurements are performed using a (Hitachi F3010) spectrophotometer with excitation at 488 nm and measuring emission at 525 nm, and values are expressed in pmoles, by extrapolation from the calibration curve constructed using known quantities of DCF, and in relation to total cellular protein. Values are thus expressed in % ages with respect to the ROS content of the cells not subjected to treatment with BSO (control) to which are assigned a value of 100.

Sample Preparation

The Extracts 1 and 2, Teupolioside and Ascorbic Acid were solubilized in phosphate buffer 10 mM at pH 7.4, whereas trolox was solubilized in 0.1% of dimethylsulphoxide and culture medium.

Results

*Ajuga reptans* Extracts 1 and 2 significantly reduce ROS concentrantion, since they are comparable to each other and more effective than isolated teupolioside phenylpropanoid, while they result more effective than Trolox and ascorbic acid.

TABLE 12

Anti-oxidating effect of *Ajuga reptans* Extracts 1 and 2 as compared with teupolioside, ascorbic acid and Trolox.

| Treatment | Concentration | % ROS in picomoles |
|---|---|---|
| Control | | 100 ± 9* |
| BSO | | 160 ± 12** |
| Extract 1 | 20 µM | 110 ± 8* |
| Extract 2 | 20 µM | 105 ± 7* |
| Teupolioside | 20 µM | 135 ± 7* |
| Ascorbic acid | 1 mM | 130 ± 10* |
| Trolox | 20 µM | 125 ± 8* |

*p > 0.05 vs BSO.
**p > 0.05 vs Control, Student's - Newman's- K - Test

EXAMPLE 11

Assessment of the Protective Activity Against Oxidative Stress Induced by Glutathione Deficiency on Fibroblast Cultures Preparation of the Cultures 3T3 fibroblasts (BALB/c mouse) are cultured in DMEM containing 20% calf foetal serum (FCS); the cells are seeded in 16 mm-diameter 24-well plates and grown for 24 hours until reaching 50% confluence. The cells were subsequently incubated with BSO 200 µM: the BSO concentration used is sufficient to induce death in more than 87% cells within 24 hours. Cell survival has been calculated by colorimetry using MTT that colours the viable cells in blue, but not dead cells or lytic debris. The solubilized reaction products are measured by means of ELISA technique: a value directly proportional to the number of viable cells is obtained. The MTT absolute value obtained is normalized by small inner differences to the absorption in relation to the value of the control cultures considered as 100% viable cells.

Solubilization of the Products

The Extracts 1 and 2, teupolioside and ascorbic acid were solubilized in phosphate buffer 10 mM at pH 7.4, then added to the culture at the desired concentrations together with BSO.

Results

BSO irreversibly inhibits the synthesis of glutathione, an endogen intracellular substance which plays a role of antioxidant and free radical scavenger: its deficiency induces oxidative stress and cell death in various cell types. The Extracts are equally active and exhibit a greater activity as compared with the control compounds and furthermore they do not exhibit cytotoxic effects at concentrations near to maximum activity.

TABLE 13

Effect of Extracts 1 and 2 compared with Teupolioside and ascorbic acid on the death of 3T3 fibroblasts by BSO-induced oxidative damage.

| Treatment | Concentration | % survived cells |
|---|---|---|
| BSO | | 9.40% |
| Extract 1 | 20 μM | 87.3% |
| Extract 2 | 20 μM | 89.6% |
| Teupolioside | 20 μM | 75.5% |
| Ascorbic acid | 1 mM | 72.3 |

In all tests, the Extracts in the different mutual proportions of phenylpropanoids exhibit overlapping biological activity, superior to isolated phenylpropanoids and markedly superior to ascorbic acid.

EXAMPLE 12

Determination of the Antimicrobial Activity by *Ajuga Reptans* Extracts, Teupolioside and Isoteupolioside To the purpose of detecting any antimicrobial activity of the *Ajuga reptans* extract and the individual phenylpropanoid isoteupoloside (FPD) and teupolioside (FPA), an assay has been prepared, generally known as multiple dilution assay, with the following microbial strains: *Pseudomonas aeruginosa* ATCC 9027; *Candida albicans* ATCC 2091. The phenylpropanoids FPD, FPA and the Extract 2 of *Ajuga reptans* were assayed at the concentrations of 0.5 mg/ml, 2 mg/ml and 5 mg/ml. The microbial strains for the test were inoculated in culture broths (in Triptone soy broth medium) containing the substances to be assayed at the concentrations described above. In parallel with these tests, culture broths containing the microbial strain alone have been prepared (controls). The culture-broths have been incubated at 30° C. for a period of 28 days. Samples of the various culture-broths have been taken at 0, 7, 14, 21 and 28 days, with the aim of counting the number of CFU/ml in relation to the various fungal strains, by plating the cultures on solid medium. A certain number of serial dilutions have been prepared for each sample in order to determine the microbial load of each culture-broth. Each dilution has been assayed in triplicate on solid medium. Then number of CFUs reported in the table is the mean of the counts performed on the triplicate assays. The results obtained are reported in the following table.

TABLE 14

Effect of the Extract 2 and isoteupolioside on the growth of *Pseudomonas aeruginosa* ATCC 9027

| Samples | T0 (CFU/ml) | T7d (CFU/ml) | T14d (CFU/ml) | T21d (CFU/ml) | T28d (CFU/ml) |
|---|---|---|---|---|---|
| Control | $1.3 \times 10^6$ | $2.8 \times 10^7$ | $>10^{10}$ | $>10^{10}$ | $>10^{10}$ |
| Extract 2 (0.5 mg/ml) | $1.1 \times 10^6$ | $1.9 \times 10^6$ | $3.5 \times 10^8$ | $2.8 \times 10^7$ | $1.5 \times 10^6$ |
| Extract 2 (2 mg/ml) | $1.5 \times 10^6$ | $1.7 \times 10^6$ | $4.2 \times 10^7$ | $7.8 \times 10^6$ | $5.2 \times 10^5$ |
| Extract 2 (5 mg/ml) | $9.8 \times 10^5$ | $1.3 \times 10^6$ | $3.4 \times 10^6$ | $3.5 \times 10^4$ | $4.5 \times 10^3$ |
| Isoteupolioside (0.5 mg/ml) | $9.6 \times 10^5$ | $1.2 \times 10^6$ | $2.1 \times 10^7$ | $2.4 \times 10^4$ | $9.8 \times 10^3$ |
| Isoteupolioside (2 mg/ml) | $5.9 \times 10^5$ | $1.1 \times 10^6$ | $1.9 \times 10^6$ | $9.2 \times 10^3$ | $9.8 \times 10^3$ |
| Isoteupolioside (5 mg/ml) | $3.6 \times 10^5$ | $9.8 \times 10^5$ | $1.1 \times 10^5$ | $2.5 \times 10^3$ | $9 \times 10^1$ |

TABLE 15

Effect of the Extract 2 and isoteupolioside on the growth of *Candida albicans* ATCC 2091

| Samples | T0 (CFU/ml) | T7d (CFU/ml) | T14d (CFU/ml) | T21d (CFU/ml) | T28d (CFU/ml) |
|---|---|---|---|---|---|
| Control | $2.2 \times 10^6$ | $3.5 \times 10^9$ | $>10^{10}$ | $>10^{10}$ | $>10^{10}$ |
| Extract 2 (0.5 mg/ml) | $1.2 \times 10^6$ | $2.8 \times 10^7$ | $1.6 \times 10^9$ | $8.3 \times 10^7$ | $6.4 \times 10^7$ |
| Extract 2 (2 mg/ml) | $2.2 \times 10^6$ | $1.2 \times 10^7$ | $9.9 \times 10^6$ | $1.2 \times 10^6$ | $1.1 \times 10^6$ |
| Extract 2 (5 mg/ml) | $9.2 \times 10^6$ | $8.3 \times 10^6$ | $9.8 \times 10^5$ | $2.4 \times 10^5$ | $1.8 \times 10^5$ |
| Isoteupolioside (0.5 mg/ml) | $9.7 \times 10^5$ | $1.7 \times 10^6$ | $5.8 \times 10^5$ | $7.3 \times 10^7$ | $6.5 \times 10^7$ |
| Isoteupolioside (2 mg/ml) | $9.1 \times 10^5$ | $1.1 \times 10^6$ | $2.3 \times 10^6$ | $1.2 \times 10^5$ | $3.8 \times 10^3$ |
| Isoteupolioside (5 mg/ml) | $8.1 \times 10^5$ | $3.1 \times 10^5$ | $8.5 \times 10^3$ | $5 \times 10^1$ | <10 |

In the anti-microbial activity test, the teupolioside exhibited an activity similar to isoteupolioside.

The data obtained from the tests allows one to deduce that phenylpropanoid isoteupolioside and teupolioside at 5 mg/ml concentration exert a significant inhibiting action in relation to the growth of *Pseudomonas aeruginosa* ATCC 9027 and *Candida albicans* ATCC 2091. The Extract 2 exerts inhibition of the growth of the two micro-organisms to a less marked extent than the isoteupolioside and teupolioside pure molecules.

With regard to their potent effect on oxidative stress, the inventive extracts and the isoteupolioside are valid tools in the prevention and treatment of disease states associated with damage due to free radicals, such as: anoxia, trauma and inflammatory based diseases of the nervous system such as cerebral stroke, cerebral and spinal trauma, haemorrhagic shock, epilepsy, cerebral ischemia and ischemic spinal injury, peripheral neuropathy and cephalalgia (B. Halliwell et al, 1992); degenerative type pathologies of the nervous system also associated with ageing or autoimmune based or having inflammatory components such as amyotrophic lateral sclerosis, multiple sclerosis, Parkinson's disease, Alzheimer's disease, senile dementia and Huntington's disease (Olanow C. W. "A Radical Hypothesis for Neurodegeneration", TINS, 1993, 16(11):439-444; Dib M. Amyotrophic lateral sclerosis: progress and prospects for treatment. Drugs 2003; 63(3):289-310); reperfusion damage and cardiovascular diseases including angina, percutaneous transluminal coronary angioplasty (PTCA), myocardial infarction and vasculopathies (Bagchi D, Sen C K, Ray S D, Das D K, Bagchi M, Preuss H G, Vinson J A. Molecular mechanisms of cardioprotection by a novel grape seed proanthocyanidin extract. Mutat Res 2003 February-March; 523-524:87-97), atherosclerosis and muscular damage (Mertens A, Verhamme P, Bielicki J K, Phillips M C, Quarck R, Verreth W, Stengel D, Ninio E, Navab M, Mackness B, Mackness M, Holvoet P. Increased low-density lipoprotein oxidation and impaired high-density lipoprotein antioxidant defence are associated with increased macrophage homing and atherosclerosis in dyslipidemic obese mice: LCAT gene transfer decreases atherosclerosis. Circulation 2003 Apr. 1; 107(12):1640-6.); dismetabolic disorders such as diabetes mellitus and the neurological, vascular and ophthalmic complications thereof (Yoshida K., Hirokawa J., Tagami S., Kawakami Y., Urata Y., Kondo T. "Weakened cellular scavenging activity against oxidative stress in diabetes mellitus: regulation of glutathione synthesis and efflux" Diabetologia, 1995 February, 38(2):201-210); toxic diseases i.e. alcoholism and its neurological complications besides liver cirrhosis (Clot P., Tabone M., Arico S., Albano E. "Monitoring oxidative damage in patients with liver cirrhosis and different daily alcohol intake" Glut., 1994 November, 35(11): 1637-43), peripheral neuropathies including toxic ones (Leonetti C, Biroccio A, Gabellini C, Scarsella M, Maresca V, Flori E, Bove L, Pace A, Stoppacciaro A, Zupi G, Cognetti F, Picardo M. Alpha-tocopherol protects against cisplatin-induced toxicity without interfering with antitumor efficacy Int J Cancer 2003 March 20; 104(2):243-50); skin and mucosal disorders such as photolysis, actinic damage, skin ageing, atopy, diseases associated with karatinocyte hyperproliferation for example psoriasis, xeroderma, skin tumours (Mittal A, Elmets C A, Katiyar S K CD11b+ cells are the major source of oxidative stress in UV radiation-irradiated skin: possible role in photoaging and photocarcinogenesis. Photochem Photobiol 2003 March; 77(3):259-64; Pinnell S R. Cutaneous photo-damage, oxidative stress, and topical antioxidant protection. J Am Acad Dermatol 2003 January; 48(1):1-19; Tsukahara H, Shibata R, Ohshima Y, Todoroki Y, Sato S, Ohta N, Hiraoka M, Yoshida A, Nishima S, Mayumi M. Oxidative stress and altered antioxidant defences in children with acute exacerbation of atopic dermatitis. Life Sci 2003 Apr. 18; 72(22):2509-16); dental disorders including bacterial infections, gingivitis; viral infections such as HIV (Greenspan and Aruoma, 1994 ref. cit.); Herpes Zoster, Herpes Simplex e Citomegalovirus; disorders of the respiratory apparatus i.e. cystic fibrosis, asthma, rhinitis including due to allergies, "respiratory distress" and neonatal pulmonary hypertension (Fortoul T I, Valverde M, Lopez Mdel C, Lopez I, Sanchez I, Avila-Costa M R, Avila-Casado Mdel C, Mussali-Galante P, Soria E, Rojas E. Nasal cytology and genotoxic damage in nasal epithelium and leukocytes: asthmatics versus non-asthmatics. Int Arch Allergy Immunol 2003 March; 130(3):232-5); articular disorders including rheumatoid arthritis (Lee S H, Chang D K, Goel A, Boland C R, Bugbee W, Boyle D L, Firestein G S. Microsatellite instability and suppressed DNA repair enzyme expression in rheumatoid arthritis. J Immunol 2003 February 15; 170(4):2214-20); tumour pathologies; ophthalmic disorders for example cataract, retinal degeneration (Organisciak D T, Darrow R M, Barsalou L, Kutty R K, Wiggert Susceptibility to retinal light damage in transgenic rats with rhodopsin mutations. Invest Ophthalmol Vis Sci 2003 February; 44(2):486-92); hearing apparatus damage (Shi X, Nuttall A L. Up-regulated INOS and oxidative damage to the cochlear stria vascularis due to noise stress. Brain Res 2003 Mar. 28; 967(1-2):1-10); diminuita risposta immune (Halliwell B et al., 1992 ref.cit.; Toyokuni S. et al. "Persistent oxidative stress in cancer" FEBS Lett., 1995 Jan. 16, 358(1): 16, 358(1): 1-3; Ames B. N., Shigenaga M. K.) lesions of the gastric, enteric (Yajima N., Hiraishi H., Harada T., "Protection of Cultured Rat gastric cells Against Oxidant Stress by Iron Chelation" Digestive Diseases and Sciences 1995, 40(4):879-886) and intestinal tract, such as Chron's disease and ulcerous colitis (Geerling, B. J., Badart-Smook, A., van Deursen, C., van Houwelingen, A. C., Russel, M. G., Stockbrugger, R. W., Brummer, R. J. "Nutritional supplementation with N-3 fatty acids and antioxidants in patients with Crohn's disease in remission: effects on antioxidant status and fatty acid profile". Inflamm. Bowel Dis. 2000 May; 6(2): 77-84).

Furthermore, in relation to their potent effectiveness against platelet aggregation as described in example 6, the inventive extracts, teupolioside and isoteupolioside are valid tools in the prevention and treatment of disease states associated with the formation of platelet clots and atheromatous plaques, besides finding use for the preservation and stabilisation of purified platelets for transfusional use.

In relation to their marked anti-inflammatory activity such as described in the example 5, anti-microbial activity (described in the example 12), the *Ajuga reptans* extracts, teupolioside and isoteupolioside of the invention are valid tools in the prevention and treatment of disease states associated with skin and cutis lesions caused by burns, incisions or lesions and mechanical trauma, diabetes sores and bedsores with facilitation of the cicatrisation and tissue repair processes. Due to the aforementioned biological activities, the extracts, teupolioside and isoteupolioside may be used as promoters of the tissue repair processes in cases of mucosal and endothelial lesions and ulcers, including those of the gastrointestinal tract and vaginal mucosa. Furthermore, the *Ajuga reptans* extracts, isoteupolioside and teupolioside can be effectively used, topically and systemically, for treating alterations of the scalp and favouring the hair vital cycle.

As a result of the high chelating activity shown in example 7, the extracts, teupolioside and isoteupolioside may be used for the treatment of numerous allergy-related pathologies, both systemic and cutaneous (for example: allergic skin reaction to $Ni^{2+}$ in topical cosmetic and pharmaceutical products). Said activity may be exploited in order to protect the body from harm caused by the presence of excess heavy metals, such as iron and copper, for example following thalassemia and other diseases with high haemosiderosis. A combination of radical scavenging, anti-oxidant and chelating activities, may form the basis for the use of *Ajuga reptans* extracts, teupolioside and isoteupolioside against disease processes caused by free radicals generated by the presence of excess heavy metals.

The *Ajuga reptans* extracts, teupolioside and isoteupolioside have a high inhibiting capacity in relation to the activities of the enzymes 5 alpha reductase, both type I and type II, and lipoxygenase, as shown in example 8. This inhibitory capacity may be exploited for the treatment and prevention of hair loss in cases of androgenetic alopecia and alopecia aereata. Furthermore, this activity may be exploited for the treatment of juvenile acne and in subjects affected by prostate diseases dependent on the activation of 5 alpha reductase.

As reported in example 9, *Ajuga reptans* extracts, teupolioside and isoteupolioside demonstrate high inhibitory activity in relation to the enzyme tyrosinase. This activity may be exploited in order to bring about bleaching effects on the skin.

The compositions with teupolioside and isoteupolioside can be also effective as dietary supplements in case of oxidative stress conditions.

While several specific examples of compositions or extracts have been set forth above in relation to particular activities, it is understood that, independently from the examples, all the extracts, teupolioside and isoteupolioside are capable of developing one or more of said therapeutic, cosmetic or nutritional activities for human, veterinary and zootechnical use.

The doses, times and routes of administration of the treatment will be selected on the basis of the type, stage, severity and location of manifestation of the pathology or nutritional state. For all the pathologies mentioned, systemic and oral administration are indicated, but additionally also topical and transdermal, and in any case so as to make the active ingredient maximally available.

For the oral formulations, administration in the form of tablets, lozenges and capsules, but also powders, suspensions and effervescent forms are preferred: for topical treatment, gels, creams, ointments and solutions compatible with dermal and mucosal use are preferred, in addition to eye washes for administration into the conjunctival sac. The injectable forms are formulated using solvents for pharmaceutical use, compatible with intravenous, intramuscular and subcutaneous administration.

The therapeutic dose varies, depending on the patients age, weight, sex and type of pathology, between 1 mg and 2.5 g per day and preferably between 5 and 250 mg per day, taken in a single dose or in 2-4 doses or in slow release form, depending on the patients therapeutic need, and however for periods of time not shorter than 30 days.

At appropriate concentrations, the same extracts, teupolioside and isoteupolioside may be formulated in the form of supplements, to be taken orally for prevention, or as aids in the treatment of changes resulting from disreactive states in humans or in veterinary medicine. The active principles at the suitable concentrations and in suitable formulations can be also used in cosmetic applications.

Thanks to the absorbance spectrum of the phenylpropanoids, which ranges from 240 nm to 350 nm (UVB absorption range), such substances may be used for the preparation of sun filters.

Some examples of pharmaceutical, cosmetic and supplement preparations are reported in the following, for the purposes of non-limiting illustration:

EXAMPLE 1

Coated Tablets for Oral Use

Active ingredient: Total extract 500 mg
Excipients: Microcristalline cellulose, carboxymethylamide, gelatin, Glycerine, Hydroxypropylcellulose, sodium laurylsulfate, yellow iron oxide, Titanium dioxide, Magnesium stearate, white wax.

EXAMPLE 2

Preparation for Injection Use

Active ingredient: Total extract 50 mg
Excipients: pH 7 buffered injectable solution, sufficient for 2 ml

EXAMPLE 3

Gel for Topical Application

Active ingredient: Total extract 100 mg
Excipients: Carboxypolymethylene, ethyl alcohol, p-hydroxybenzoic acid esters, neroli oil, preserving agents, sufficient water.

EXAMPLE 4

Soluble Preparation—Dietary Supplement

Active ingredient: Total extract 100 mg Magnesium, Selenium, Folic Acid
Excipients: Anti-caking agents: silicon dioxide;
Sweeteners: saccharin sodium, aspartame, Guaranteed content yeast
Colouring agent: beta-carotene;
Acidulants: citric acid; orange flavour.
The *Ajuga reptans* extracts may be formulated for use in the veterinary sector and as dietary supplements for zootechnical use, such as, as a non-limiting example, for the raising of fowl and fish.

From the above description, it is understood that the *Ajuga reptans* extracts, teupolioside and isoteupolioside for use in the preparation of drugs, cosmetics or nutritional substances, both human and zootechnical, advantageously allow the provision of compounds capable of having unexpectedly greater antioxidant activity, in some cases, with respect to any individual phenylpropanoid.

In addition, said Extracts, teupolioside and isoteupolioside can be advantageously used as cicatrizers and for mucosal tissue repair. Obviously, one skilled in the art, with the aim of satisfying contingent and specific needs, can bring about a number of modifications and variations to the plant cell extract for the uses outlined above, all however contemplated within the scope of the invention as defined in the following claims.

The invention claimed is:
1. A pharmaceutical or cosmetic composition comprising:
a physiologically acceptable medium; and
an extract derived in part according to an in-vitro plant cell culture method from an isolated plant cell line of *Ajuga reptans* IRBN22 (DSM 16451) derived from undifferentiated callus tissues;
wherein the extract comprises a chromophore free fraction and phenylpropanoids comprising isoteupolioside;
the pharmaceutical or cosmetic composition comprising isoteupolioside in a sufficient amount to exhibit a pharmacological or cosmetic activity of at least one of the group selected from an anti-oxidant activity, a platelet aggregation activity, and anti-inflammatory activity, an anti-lipoxygenase activity, an anti-5-alpha-reductase activity, an anti-tyrosinase activity, an anti-fungal activity and a metal-chelating ($Fe^{2+}$, $Fe^{3+}$, $Cu^{2+}$ e $Ni^{2+}$) activity; and the isoteupolioside is represented by a general formula (I):

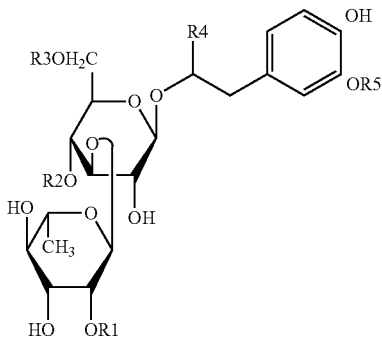

wherein R1 is galactose, R2 is hydrogen, R3 is caffeic acid, R4 is a hydrogen atom and R5 is a hydrogen atom.

2. The pharmaceutical or cosmetic composition according to claim 1, wherein the extract comprises:

from 20% to 90% by weight phenylpropanoids; and from 80 to 10% of the chromophore-free fraction comprising oligo- and polysaccharide, protein and lipid molecules.

3. The pharmaceutical or cosmetic composition according to claim 1, wherein the extract comprises:

between 30% and 60% by weight phenylpropanoids; and between 70% and 40% of said chromophore-free fraction.

4. The pharmaceutical or cosmetic composition according to claim 2, wherein the phenylpropanoids comprise between 5% and 25% by weight isoteupolioside with respect to the total mass of phenylpropanoids.

5. The pharmaceutical or cosmetic composition according to claim 2, wherein the phenylpropanoids comprise between 30% and 65% by weight isoteupolioside with respect to the total mass of phenylpropanoids.

6. A pharmaceutical or cosmetic composition comprising:

an extract having a chromophore-free fraction and phenylpropanoids;

the extract being derived in part from an isolated plant cell line of *Ajuga reptans* IRBN22 (DSM 16451) and comprising 20% to 80% by weight of phenylpropanoid isomers represented by a general formula (I):

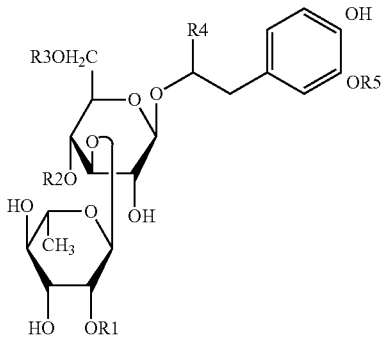

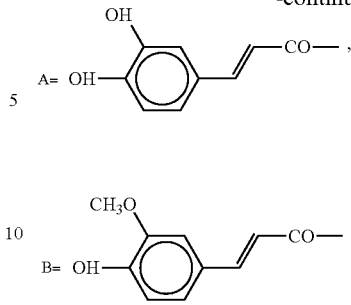

wherein:
R1 is a hydrogen atom or a monosaccharide with 5 or 6 carbon atoms or a disaccharide with 10 to 12 carbon atoms;

R2 is a hydrogen atom or is a caffeoyl (A) group or a feruloyl (B) group;

R3 is a hydrogen atom or a monosaccharide with 5 or 6 carbon atoms or a disaccharide with 10 to 12 carbon atoms or is a caffeoyl (A) group or a feruloyl (B) group;

R4 is a hydrogen atom, or a linear or branched alkyl group with 1 to 3 carbon atoms or a hydroxyl;

R5 is a hydrogen atom, or a linear or branched alkyl group with 1 to 3 carbon atoms wherein;

when R3 is a caffeoyl (A) group or a feruloyl (B) group, then R2 is always a hydrogen atom;

when R2 is a caffeoyl (A) group or a feruloyl (B) group, then R3 is always a hydrogen atom, and R4 and R5 may be either same or different.

7. The pharmaceutical or cosmetic composition according to claim 1, wherein the isolated plant cell line is a stabilised cell lines of *Ajuga reptans*.

8. A formulation comprising plant cell extract as an active ingredient in association with a pharmaceutically or cosmetically acceptable excipient, and the extract being obtained according to a process comprising the following sequence steps:

a) obtaining a biomass of plant cells derived from a selected plant cell line of *Ajuga reptans* IRBN22 (DSM 16451);

b) facilitating an isomerisation of teupolioside into isoteupolioside having a general formula (I):

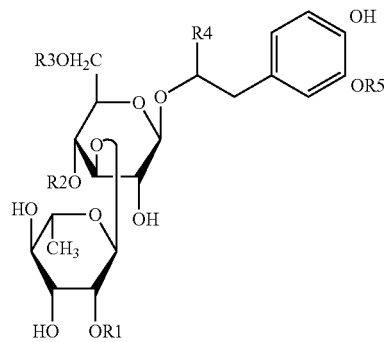

by subjecting the biomass to a thermal enzyme deactivating treatment at a temperature of 50-150° C. for 5 to 30 minutes, wherein R1 is galactose, R2 is hydrogen, R3 is caffeic acid; R4 is a hydrogen atom and R5 is a hydrogen atom; then c) recovering the extract from the biomass and forming the extract to comprise at least 20% by weight of phenylpropanoids, and a chromophore-free fraction facilitating increasing an action of the phenylpropanoids of the extract; and the phenylpropanoids comprising between 30% and 65% of isoteupolioside with respect to a total mass of the phenylpropanoids.

9. The formulation according to claim 8 wherein the formulation is used for systemic, parenteral, oral, rectal, inhalatory, topical, transdermal, intravenous, intramuscular or subcutaneous administration.

10. The formulation according to claim 9, wherein the formulation is used for oral administration is represented by tablets, lozenges, capsules, powders, solutions, suspensions or a nebulised form.

11. The formulation according to claim 9 wherein the formulation is used for administration by inhalation is represented by powders, solutions and suspensions.

12. The formulation according to claim 9, wherein the formulation is used for topical administration is an emulsion, gel or compatible solutions for dermal and mucosal use and eye washes.

13. A nutritional additive derived in part from an extract from a selected plant cell line of *Ajura reptans* IRBN22 (DSM 16451) derived from selected undifferentiated callus tissues;

facilitating an isomerisation of teupolioside into isoteupolioside having a general formula (I), indicated below, by subjecting a biomass of cells derived from the selected plant cell line to a thermal enzyme deactivating treatment;

the nutritional additive comprising:
a physiologically acceptable medium; and
between 20% and 90% by weight, over the total dry weight of said extract, of phenylpropanoids selected from the group consisting of teupolioside, methylteupolioside, isoteupolioside and mixtures thereof, and the phenylpropanoid isoteupolioside has the general formula (I):

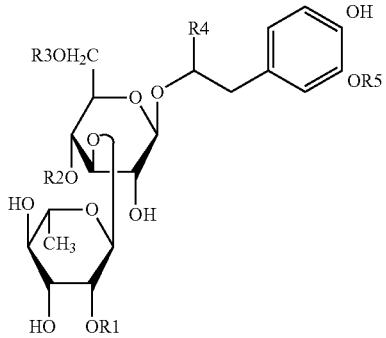

wherein R1 is galactose, R2 is hydrogen, R3 is caffeic acid, R4 is a hydrogen atom and R5 is a hydrogen atom; and the extract comprises between 80% and 10% by weight, over the total dry weight of the extract, of a chromophore-free fraction.

14. A composition comprising:
a physiologically acceptable medium; and
an extract having a chromophore-free fraction facilitating increasing an action of the extract; and
an isoteupolioside compound of a general formula (I):

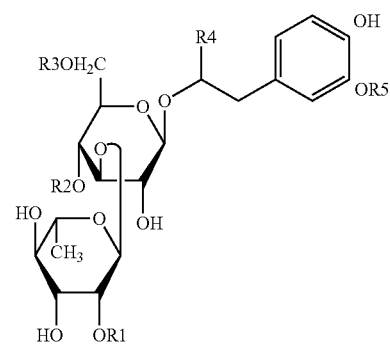

wherein R1 is a hydrogen atom or a monosaccharide with 5 or 6 carbon atoms or a disaccharide with 10 to 12 carbon atoms;

R2 is a hydrogen atom or is a caffeoyl (A) group or a feruloyl (B) group;

R3 is a hydrogen atom or a monosaccharide with 5 or 6 carbon atoms or a disaccharide with 10 to 12 carbon atoms or is a caffeoyl (A) group or a feruloyl (B) group;

R4 is a hydrogen atom, or a linear or branched alkyl group with 1 to 3 carbon atoms or a hydroxyl;

R5 is a hydrogen atom, or a linear or branched alkyl group with 1 to 3 carbon atoms;

when R3 is a caffeoyl (A) group or a feruloyl (B) group, then R2 is always a hydrogen atom;

when R2 is a caffeoyl (A) group or a feruloyl (B) group, then R3 is always a hydrogen atom;

R4 and R5 may be either same or different; and the composition comprises the isoteupolioside compound in sufficient amounts to exhibit a pharmacological or cosmetic activity of at least one of the group selected from a platelet aggregation activity, an anti-oxidating activity, an anti-inflammatory activity, an anti-tyrosinase activity, an anti-lipoxygenase activity, an anti-5-alpha-reductase activity, an anti-fungal activity and a metal-chelating ($Fe^{2+}$, $Fe^{3+}$, $Cu^{2+}$ e $Ni^{2+}$) activity.

* * * * *